United States Patent [19]

Young

[11] Patent Number: 4,627,839

[45] Date of Patent: Dec. 9, 1986

[54] PATIENT CONTROLLED ANALGESIA CONVERSION

[75] Inventor: Joe W. Young, Laguna Hills, Calif.

[73] Assignee: American Hospital Supply Corporation, Deerfield, Ill.

[21] Appl. No.: 800,281

[22] Filed: Nov. 21, 1985

[51] Int. Cl.⁴ .............................................. A61M 5/00
[52] U.S. Cl. ..................................... 604/121; 604/131; 604/154; 128/DIG. 12
[58] Field of Search ............... 604/118, 124, 110, 111, 604/151, 152, 154, 131; 417/374; 128/DIG. 12, DIG. 13

[56] References Cited

U.S. PATENT DOCUMENTS

| | | | |
|---|---|---|---|
| 4,091,810 | 5/1978 | Lundquist | 604/152 X |
| 4,424,720 | 1/1984 | Bucchianeri | 604/155 X |
| 4,435,173 | 3/1984 | Siposs et al. | 604/155 |
| 4,565,542 | 1/1986 | Berg | 604/131 |

Primary Examiner—Stephen C. Pellegrino
Attorney, Agent, or Firm—Weissenberger and Peterson

[57] ABSTRACT

A removable cover for converting a programmable infusion pump into a patient-controlled analgesia (PCA) device. The cover can be placed onto an infusion pump and electrically connected thereto when open. The cover includes an internal switch which allows selection of normal or PCA pump operation. A second internal switch automatically disables the keyboard of the pump when the cover is closed. The cover is lockable, and when it is closed and locked, the internal switches are inaccessible, the cover cannot be removed from the pump, and the electrical connection to the pump cannot be disconnected. When closed, the cover also defines an inaccessible compartment for the storage of medication. An external push button is provided to allow the patient to trigger analgesia doses at safe intervals when the pump is in the PCA mode.

4 Claims, 7 Drawing Figures

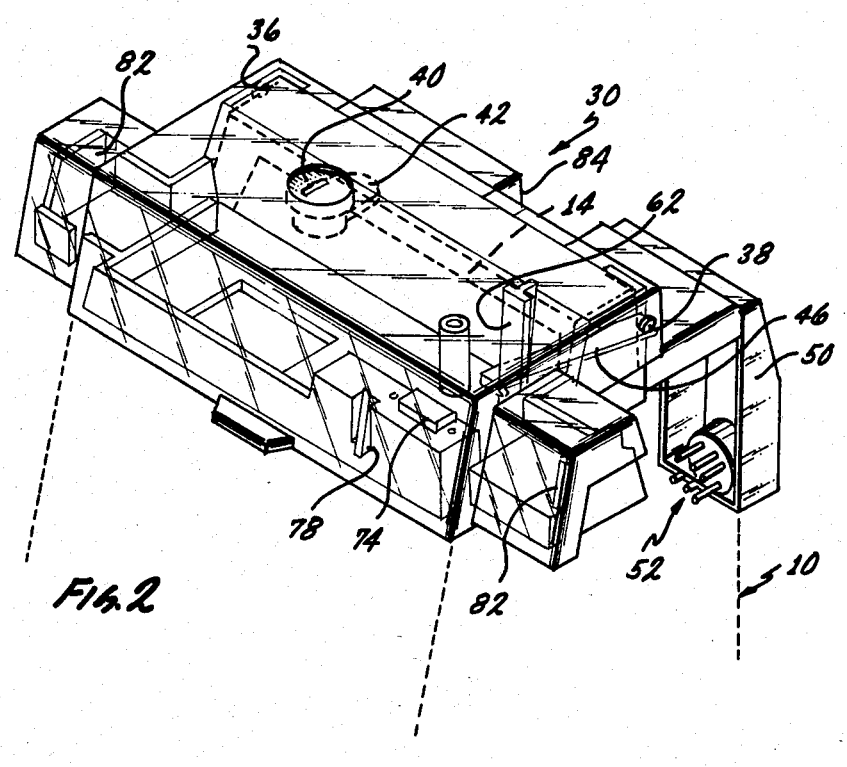
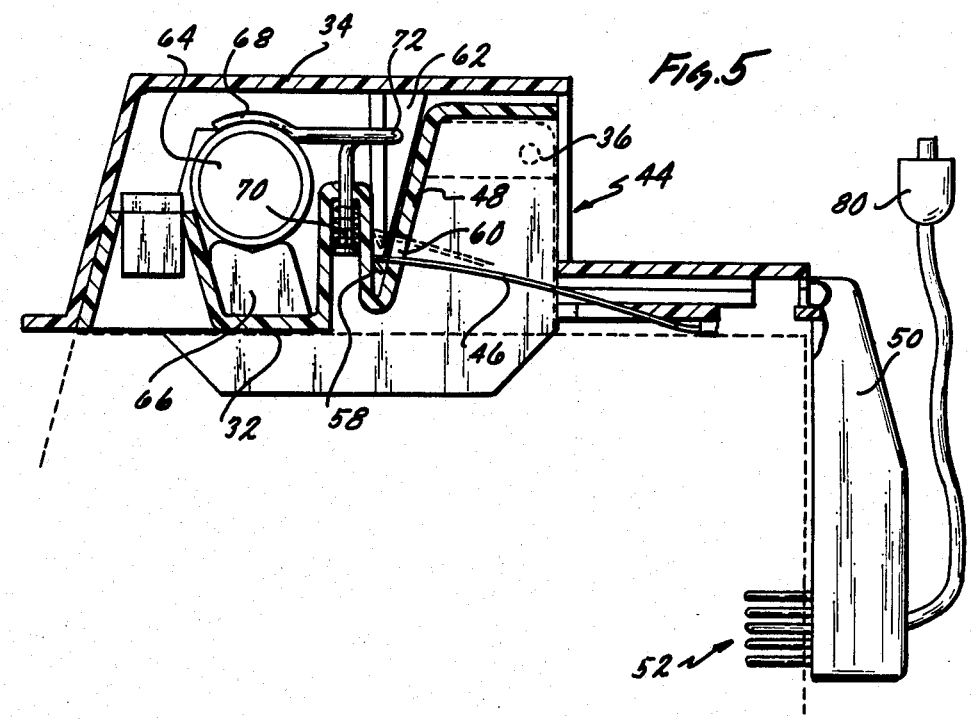

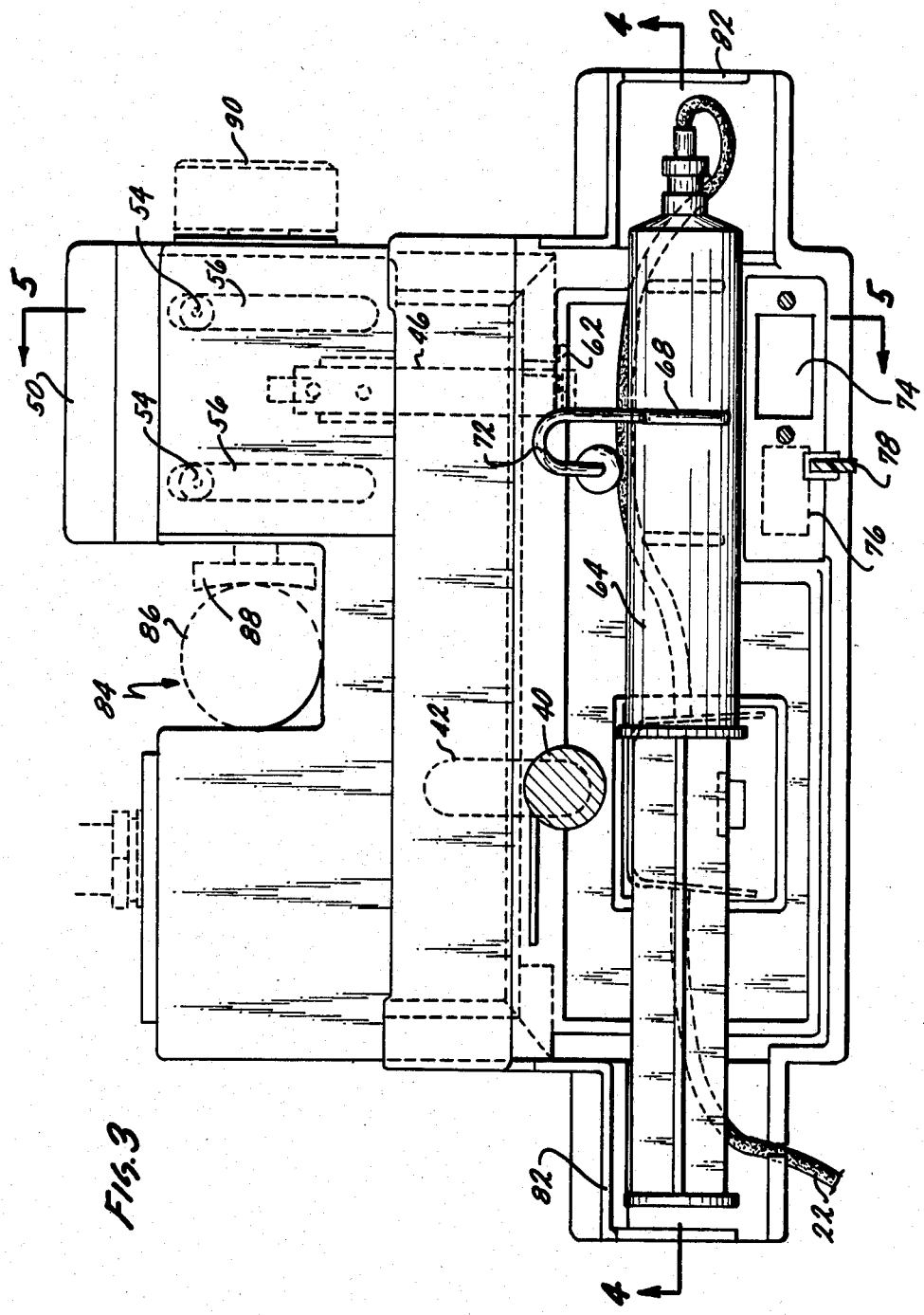

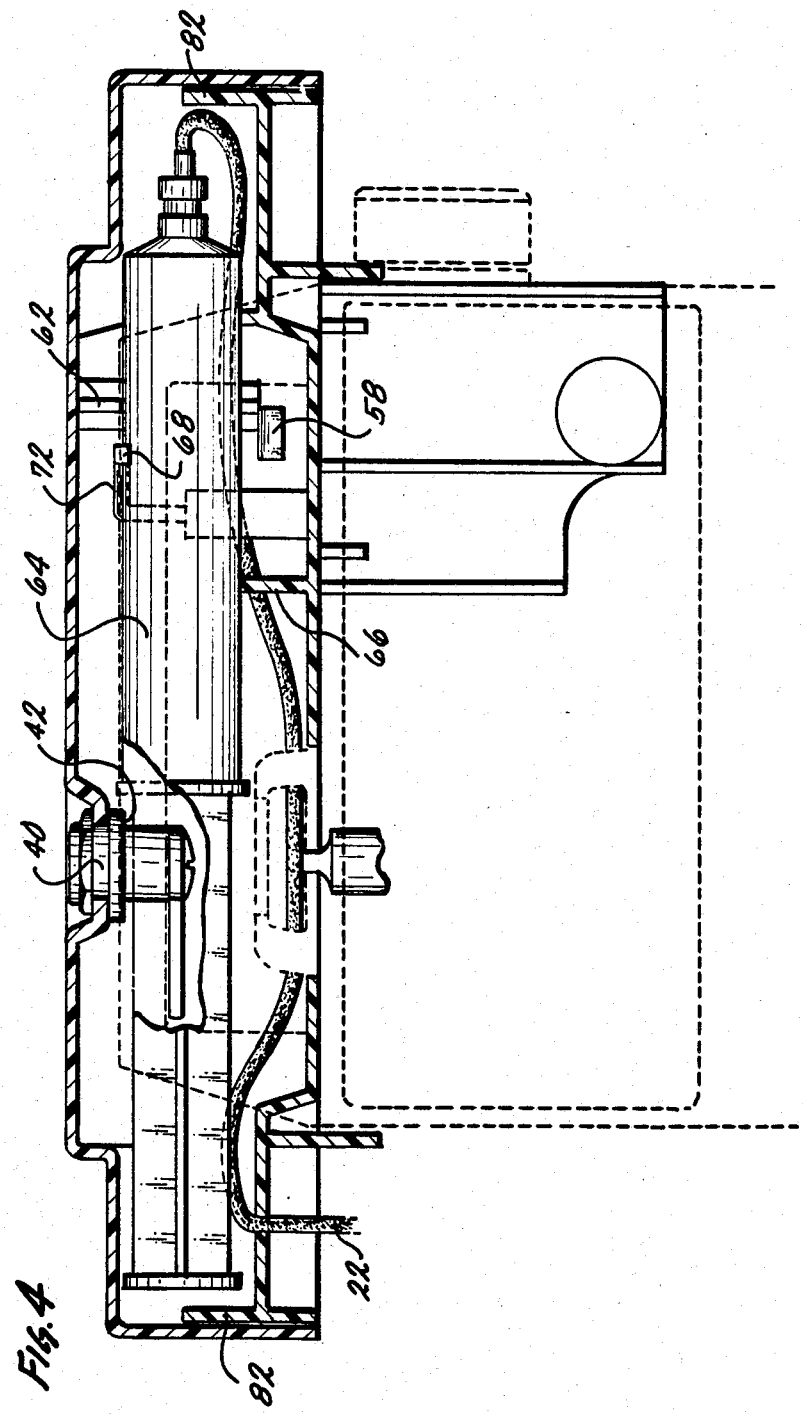

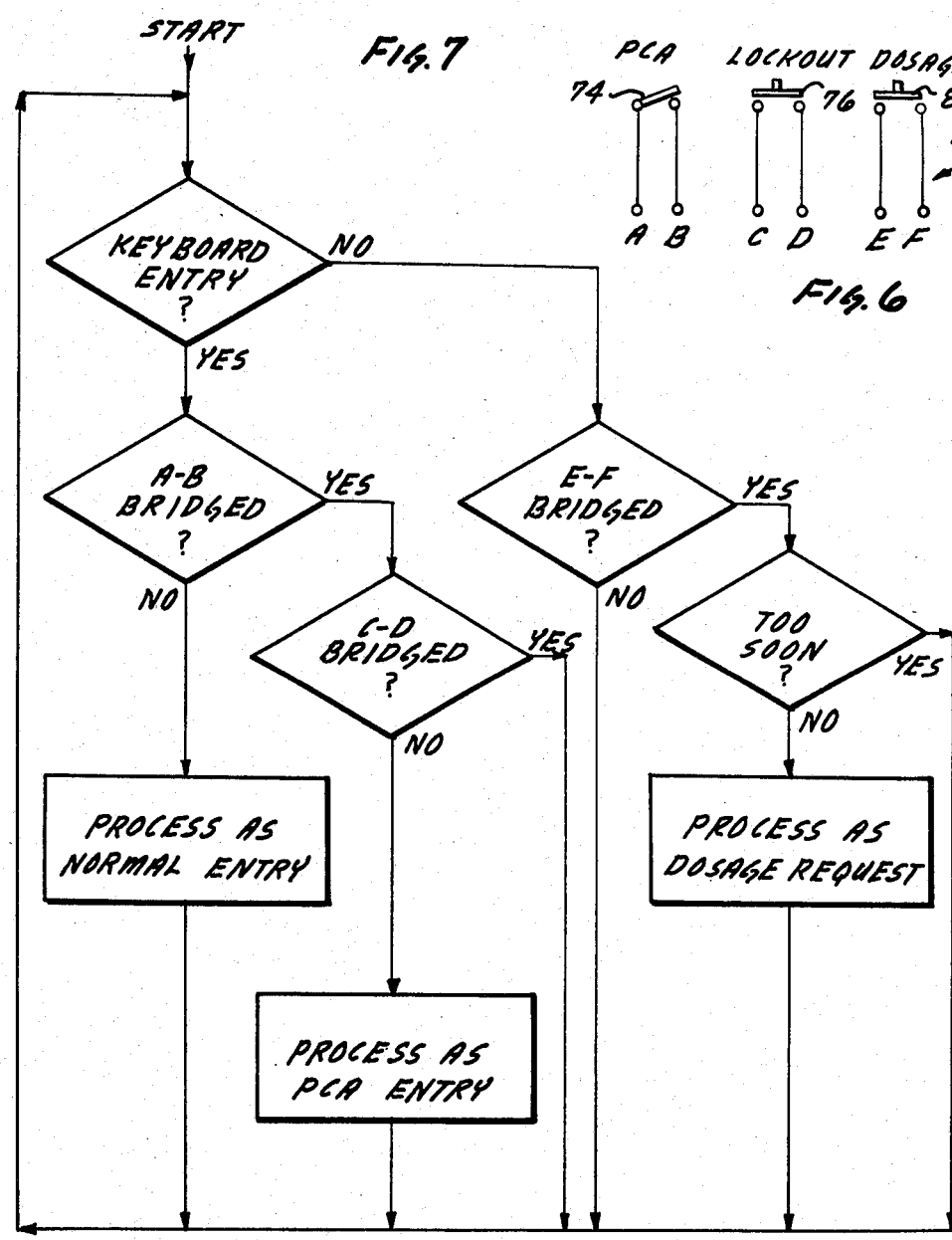

PATIENT CONTROLLED ANALGESIA CONVERSION

This invention relates to programmable infusion pumps, and more particularly to an accessory for converting a programmable infusion pump into a patient-controlled analgesia device.

BACKGROUND OF THE INVENTION

Programmable infusion pumps are widely used in the intravenous administration of medication to patients in hospitals and elsewhere. They provide accurate long term medication without the need for constant nursing supervision.

It is frequently desirable to administer analgesic medication to a patient only when the patient deems it absolutely necessary. In order to do this without recourse to a nurse, special equipment has been developed by which the patient can trigger a predetermined infusion of analgesic medication at limited intervals.

Inasmuch as infusion pumps are fairly expensive items, it is desirable to provide an accessory which can convert an ordinary programmable infusion pump into a patient-controlled analgesia (PCA) device without the need of a separate pump for PCA purposes.

SUMMARY OF THE INVENTION

The invention provides a converter which can be placed on an infusion pump and can be attached thereto by a locking device. In the preferred embodiment, the converter has a hinged cover which releases the converter from the infusion pump when the cover is open, but secures it to the pump when it is closed.

The converter can be electrically connected to the pump and carried on its inside (in a position inaccessible when the cover is closed) a selector switch which allows the pump program to be switched between normal and PCA operation, and a lockout switch which automatically disables the keyboard of the infusion pump when the cover is closed. A dosing button mounted on a cable extending from the converter allows the patient to initiate doses of analgesic medication.

In order to prevent any tampering with the pump when it is in the PCA mode, the electrical interconnection between the converter and the pump is so arranged that it cannot be disconnected when the cover is closed. Also, the medication supply for the analgesia can be placed into a compartment of the converter which is inaccessible when the converter is closed and locked.

It is therefore the object of the invention to provide an accessory by which a programmable infusion pump can be converted into a PCA device.

It is another object of the invention to provide an accessory of the type described which allows the physician full use of the pump in either normal or PCA mode, yet prevents access by the patient to the pump's programming features or to the source of analgesic medication when the pump is unattended.

BRIEF DESCRIPTION OF THE DRAWINGS

FIG. 2 is a perspective view of the converter of this invention;

FIG. 3 is a plan view of the converter with its cover removed;

FIG. 4 is a vertical section along line 4—4 of FIG. 3;

FIG. 5 is a vertical section along line 5—5 of FIG. 3;

FIG. 6 is a diagram illustrating the operation of the electrical components of the converter; and FIG. 7 is a flow chart of the microprocessor functions of the infusion pump affected by the electrical components of the converter.

DESCRIPTION OF THE PREFERRED EMBODIMENT

Figure 1:
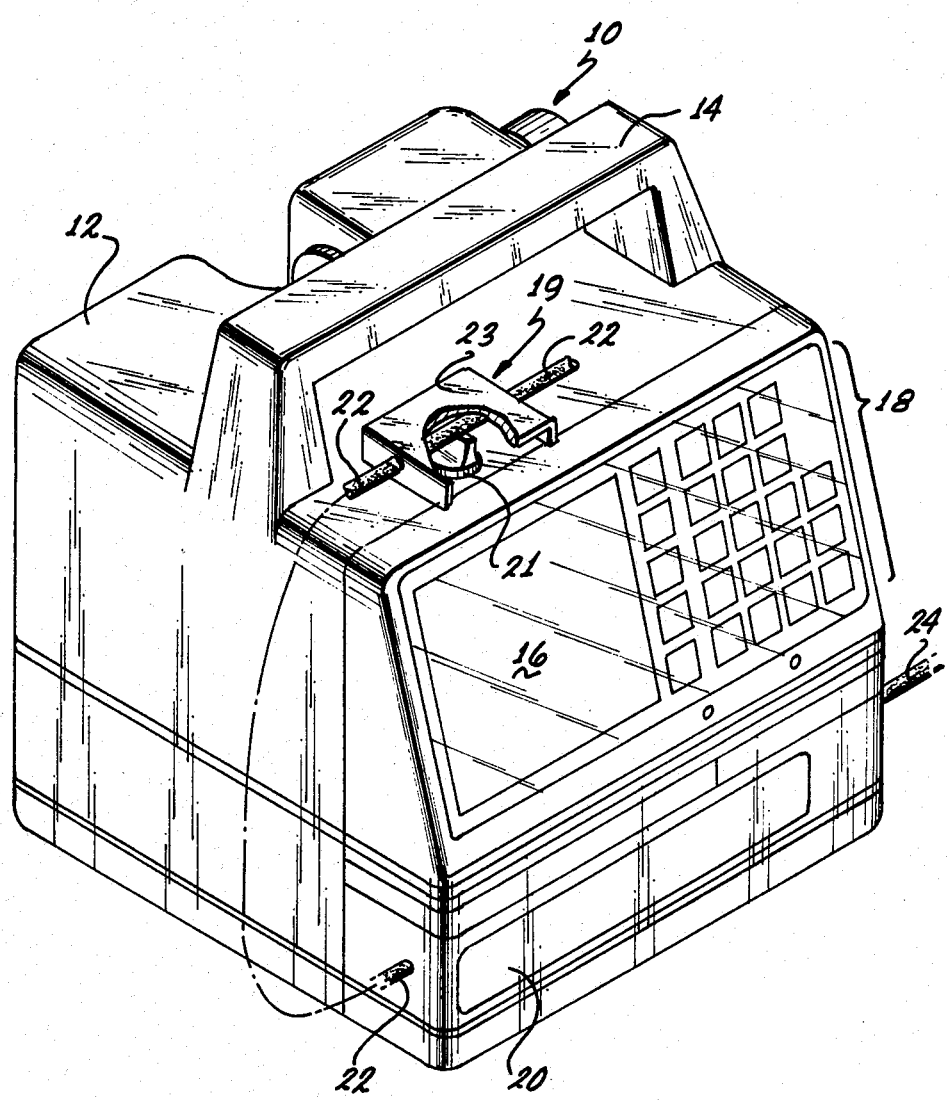
FIG. 1 is a perspective view of the infusion pump with which the converter of this invention is used.

FIG. 1 shows a typical microprocessor-controlled infusion pump of the type with which the converter of this invention can be used. The pump 10 includes a housing 12 integrally formed with a carrying handle 14. The front face of the pump 10 may typically contain a data display screen 16 and a keyboard 18 which may be used to program various infusion parameters in a conventional manner. A pumping mechanism located behind an access door 20 pumps precisely measured quantities of fluid from a supply cannula 22 to an output cannula 24 which is connected to the patient.

The pump 10 is preferably equipped with a safety shutoff 19 through which the supply cannula 22 is threaded. A vertically movable shutoff bar 21 squeezes the cannula 22 against a retaining plate 23 whenever air is present in the cannula, or the pump 10 is not pumping, so as to avoid any accidental discharge of fluid if the supply cannula becomes disconnected.

In normal operation, the pump 10 is typically used to automatically infuse IV fluid and/or medication at a controlled rate over an extended period of time. However, in some instances, it is advisable to allow a patient to administer analgesia to himself in controlled quantities at controlled intervals without the intervention of a nurse. For this purpose, the microprocessor of pump 10 may be programmed by conventional techniques to dispense a selected quantity of analgesic fluid each time a control circuit is closed by the patient. To avoid excessive use of this feature, the microprocessor may render the patient-operated control inoperative for a predetermined time after each operation.

The present invention provides a convenient way to temporarily convert the pump 10 from a normal infusion pump into a patient-controlled analgesia (PCA) device when needed, thus saving the purchaser the expense of buying two separate infusion pumps for normal use and for PCA use.

As shown in FIG. 2, the conversion unit of this invention is a preferably transparent converter 30 which fits over the top of pump 10. The converter 30 has a base 32 (FIG. 5) to which a cover 34 is pivotally secured at 36, 38. When the cover 34 is closed, a key lock 40 in the cover 34 can be turned to cause a tongue 42 to engage the underside of handle 14 and thereby secure the converter 30 to the pump 10 in the closed position.

The rear of the cover 34 is open at 44 (FIG. 5) to allow access to the handle 14 and the connector latch 46, but access to the front portion of the converter 30 through the rear opening 44 is prevented by the inclined panel 48 of the base 32.

Electrical connections between the converter 30 and the pump 10 are established by a connector 50 which carries a set of pins 52 adaptedd to engage a matching socket (not shown) in the rear wall of the pump 10. The connector 50 is slidably mounted on the base 32 by stubs 54 and guides 56, as best shown in FIG. 3. When the converter 30 is in place and the pins 52 are fully inserted in the electrical socket of pump 10, the nose 58 of the resilient connector latch 46 engages the front side of the panel 48 below the slot 60 and prevents disengagement of the connector 50 from the pump 10 until the latch 46 is lifted up by hand. When the cover 34 is closed, a finger 62 holds nose 58 in engagement with panel 48 so that the connector 50 cannot be disengaged while the cover 34 is closed.

The analgesic medication is contained in a syringe 64 which rests on supports 66 formed in the base 32. The syringe 64 is held in place by a spring-loaded, swingable arm 68 which can be lifted and turned against the action of spring 70 by grasping its U-shaped portion 72.

The supply cannula 22 is placed so as to extend from the tip of syringe 64 through the safety shutoff 19 into the pump 10. It will be noted that when the cover 34 is closed, neither the syringe 64 nor any portion of the cannula 22 lying upstream of the safety shutoff 19 is accessible. This prevents theft of the medication (often morphine or other substances attractive to drug addicts) while not authorized personnel is present.

Three electrical controls are associated with the converter of this invention. One is the PCA switch 74 which is manually operable between an open "NORMAL" and a closed "PCA" position; one is the lockout microswitch 76 (FIG. 3) which is closed by the finger 78 on the cover 34; and the third is the dosing button 80 which the patient presses to receive a dose of analgesia.

The PCA switch 74 allows the medical personnel to use the pump 10 as a normal infusion pump, if desired, without removing the converter 30. The lockout microswitch 76 disables the keyboard controls 18 on the face of the pump 10 when the cover 34 is closed, so that the pump settings cannot be changed except by authorized personnel. The dosing button 80 can be freely pressed as desired by the patient, but the microprocessor, as discussed hereafter, will not allow a dose to be dispensed unless a pre-selected time interval has elapsed since the last dose.

FIGS. 6 and 7 illustrate the electrical operation of the converter 30. The microprocessor program of pump 10 (which contains both normal infusion and PCA functions) cycles continuously while the pump 10 is powered. If a keyboard entry has been made and the PCA switch 74 is open, the keyboard entry is conventionally processed as a command relating to the normal infusion portion of the microprocessor program. If a keyboard entry has been made but the PCA switch 74 is closed, the entry is interpreted and processed as a command for the PCA portion of the microprocessor program unless lockout microswitch 76 is also closed. If it is, then the keyboard entry is ignored.

If the dosing button 80 is closed while no keyboard entry is in progress, the microprocessor program first checks its clock counter to see if sufficient time has elapsed since the last dose. If it has, the program initiates the administration of a dose; if not, the dosing request is ignored.

The edges of the cover 34 overlap raised edges 82 of the base 32 around the syringe 64 to prevent the cover 34 from being pried open. At its rear, the base 32 has a recess 84 to allow the pump 10 to be mounted on IV pole 86 by a clamp 88. The clamp 88 may be operated through a knob 90 of the pump 10 in the conventional manner.

Transparency of at least the cover 34 is desirable to observe the amount of medication remaining in the syringe 64, as well as the setting of the PCA switch 74.

It will be seen that the present invention provides a convenient yet tamperproof way of making a single infusion pump usable alternatively as a normal pump or a PCA pump. In addition, the present invention makes it convenient to move a single PCA attachment from one infusion pump to another as desired.

I claim:

1. An accessory for converting a programmable infusion pump to a patient-controlled analgesia device, comprising:
    (a) a converter shaped to fit on said pump, said converter having a cover portion movable between an open position in which said converter is releasable from said pump and a closed position in which said converter can be secured to said pump;
    (b) lockout switch means on said converter for preventing modification of the program of said infusion pump when said cover portion is closed, said lockout switch means being inaccessible when said cover portion is closed;
    (c) dosing switch means attached to said converter for triggering operation of said pump under patient control, said dosing switch means being accessible when said cover portion is closed;
    (d) connector means on said converter for electrically connecting said switch means to said pump;
    (e) connector latching means for releasably holding said connector means in engagement with said pump, said latching means being inoperable to release said connector means when said cover portion is closed; and
    (f) locking means for selectively locking said cover portion into said closed position and to secure said converter to said pump.

2. The accessory of claim 1, further comprising:
    selector switch means on said converter for selectively manually modifying the program of said infusion pump, said selector switch means being inaccessible when said cover portion is closed.

3. The accessory of claim 1, in which said converter defines a medication compartment, said compartment being inaccessible when said cover portion is closed.

4. The accessory of claim 1, in which said connector means are mounted on said converter for movement between a disconnected position in which said latching means is released, and a connected position in which said latching means is engaged.

* * * * *